(12) United States Patent
Schmitz et al.

(10) Patent No.: US 9,949,940 B2
(45) Date of Patent: Apr. 24, 2018

(54) PHARMACEUTICAL COMPOSITIONS CONTAINING DEXKETOPROFEN AND TRAMADOL

(71) Applicant: LABORATORIOS MENARINI SA, Badalona (ES)

(72) Inventors: Reinhard Schmitz, Berlin (DE); Tobias Kohl, Berlin (DE)

(73) Assignee: Labortorios Mena Rini SA, Badalona (ES)

( * ) Notice: Subject to any disclaimer, the term of this patent is extended or adjusted under 35 U.S.C. 154(b) by 0 days.

(21) Appl. No.: 14/767,424

(22) PCT Filed: Feb. 6, 2014

(86) PCT No.: PCT/EP2014/052342
§ 371 (c)(1),
(2) Date: Aug. 12, 2015

(87) PCT Pub. No.: WO2014/124862
PCT Pub. Date: Aug. 21, 2014

(65) Prior Publication Data
US 2015/0374650 A1 Dec. 31, 2015

(30) Foreign Application Priority Data
Feb. 14, 2013 (IT) .............................. MI2013A0210

(51) Int. Cl.
| A61K 9/42 | (2006.01) |
| A61K 31/192 | (2006.01) |
| A61K 31/135 | (2006.01) |
| A61K 9/20 | (2006.01) |
| A61K 9/28 | (2006.01) |
| A61K 9/16 | (2006.01) |
| A61K 31/133 | (2006.01) |
| A61K 47/36 | (2006.01) |

(52) U.S. Cl.
CPC .......... *A61K 31/192* (2013.01); *A61K 9/1682* (2013.01); *A61K 9/2054* (2013.01); *A61K 9/2059* (2013.01); *A61K 9/284* (2013.01); *A61K 9/2853* (2013.01); *A61K 9/2866* (2013.01); *A61K 31/133* (2013.01); *A61K 31/135* (2013.01); *A61K 47/36* (2013.01)

(58) Field of Classification Search
CPC .................................................. A61K 31/192
USPC ........................................................ 424/472
See application file for complete search history.

(56) References Cited

U.S. PATENT DOCUMENTS

| 5,516,803 A * | 5/1996 | Raffa ..................... A61K 31/19 514/570 |
| 6,596,311 B1 * | 7/2003 | Dobetti ................ A61K 9/0056 424/400 |
| 2011/0257134 A1 * | 10/2011 | Buschmann ......... A61K 31/135 514/158 |

FOREIGN PATENT DOCUMENTS

| WO | WO 2008/092219 A2 | 8/2008 |
| WO | WO 2008/150324 A1 | 12/2008 |

OTHER PUBLICATIONS

Barbanoj (Clin Pharmacokinet 2001; 40 (4): 245-262).*
Merriam-Webster (https://www.merriam-webster.com/dictionary/mix; accessed Jan. 6, 2017).*
International Search Report of PCT/EP2014/052342 dated Apr. 24, 2014.
Miranda et al., "Effects of tramadol and dexketoprofen on analgesia and gastrointestinal transit in mice," Fundamental & Clinical Pharmacology, (2009) 23: 81-88.

* cited by examiner

*Primary Examiner* — Devang K Thakor
(74) *Attorney, Agent, or Firm* — Arent Fox LLP

(57) ABSTRACT

A pharmaceutical composition as a solid oral dosage form is described, comprising:
i) a combination of two pharmacological active principles, dexketoprofen salt with an organic or inorganic base and tramadol salt with an organic or inorganic acid, wherein:
  the organic or inorganic base is selected in the group: trometamol, trimethylamine, dimethylamine, ethylamine, triethylamine, diethylamine, L-lysine, L-arginine, diethanolamine, sodium hydroxide, calcium hydroxide
  the organic or inorganic acid is selected in the group: hydrochloric, hydrobromic, phosphoric, sulfuric, methanesulfonic, benzenesulfonic, toluenesulfonic, acetic, propionic, malic, maleic, succinic, citric, L-tartaric, lactic, malonic, aspartic, glutamic;
ii) microcrystalline cellulose as a filler;
iii) a binder selected in the group: maize starch, pregelatinized maize starch, hypromellose or their mixtures;
iv) pharmaceutically acceptable excipients.

21 Claims, 5 Drawing Sheets

Figure 1

A) Dexketoprofen TRIS

B) Tramadol HCl

Figure 2

A) Dexketoprofen TRIS

B) Tramadol HCl

Figure 3

A) Dexketoprofen TRIS

B) Tramadol HCl

Figure 4

A) Dexketoprofen TRIS

B) Tramadol HCl

Figure 5

A) Dexketoprofen

B) Tramadol

PHARMACEUTICAL COMPOSITIONS CONTAINING DEXKETOPROFEN AND TRAMADOL

CROSS-REFERENCE TO RELATED APPLICATIONS

This application is a National Stage entry of International Application No. PCT/EP2014/052342, filed Feb. 6, 2014, which claims priority to Italian Patent Application No. MI2013A000210, filed Feb. 14, 2013. The disclosures of the prior applications are hereby incorporated in their entirety by reference.

FIELD OF THE INVENTION

The invention relates to a stable pharmaceutical formulation comprising the combination of the two active pharmaceutical ingredients dexketoprofen and tramadol in a solid oral dosage form with immediate release of both active ingredients.

STATE OF THE ART

Dexketoprofen is the S-(+) enantiomer of the well known, non-steroidal anti-inflammatory drug (NSAID) and reversible cyclooxygenase (COX) inhibitor, ketoprofen, with the chemical name S-(+)-2-(3-benzoylphenyl)propionic acid. Racemic ketoprofen is used as an analgesic and anti-inflammatory agent and these effects are due to the S-(+) enantiomer (dexketoprofen), while the R-(−) enantiomer does not contribute to these activities. The tromethamine salt of dexketoprofen is registered as 12.5 mg and 25 mg film-coated immediate release oral tablets in EU countries and in several non-European countries for the symptomatic treatment of acute pain of mild to moderate intensity such as musculo-skeletal pain, dysmenorrhoea and dental pain.

Tramadol is the centrally acting opioid analgesic agent (1RS,2RS)-2-[(Dimethylamino)methyl]-1-(3-methoxyphenyl)cyclohexanol. Tramadol is in the market since 1977 (Tramal®, Grünenthal). For oral use, tramadol is available as 50-300 mg capsules, tablets and sustained release formulations. Tramadol hydrochloride is the active ingredient of products with marketing authorizations in many EU countries, such as Contramal® (Italy), Adolonta® (Spain), Tramal® and Tramundin® (Germany). In addition, it is marketed in combination with other active ingredients in preparations such as Zaldiar® containing 37.5 mg tramadol hydrochloride and 325 mg paracetamol.

The combination of analgesics has been the subject of numerous studies. The combination of a NSAID with an opioid was studied in the case of ibuprofen with oxycodon and ibuprofen with codeine. The combination of 400 mg ibuprofen and 5 mg oxycodon hydrochloride is marketed in the United States as Combunox® (Forest Pharmaceuticals, Inc.). As reported by Raffa et. al. in the U.S. Pat. No. 5,516,803, the combination of tramadol and ibuprofen is synergistic for the treatment of pain and tussive conditions. The respective weight ratios were specified in the claims as 1:1 to 1:200 with the preferred ratios of about 1:2 to about 1:20.

In the publication by Tuncer et al. (Eur J Gynaecol Oncol. 2003; 24(2):181-4.), it was shown that clinically, ketoprofen seems to reduce morphine requirements by 33 to 40% with ketoprofen supposed central mechanism of analgesia when administered intravenously. According to Siyam et al. in Anesthesiology 2003; 99: A996, the co-administration of tramadol and ketoprofen produced marked antinociceptive synergy and reduced side-effects The rationale for developing an oral fixed combination of dexketoprofen and tramadol lies in the following considerations:

1. Dexketoprofen and tramadol have different mechanisms of action, the former exerts its anti-nociceptive activity mainly at peripheral level, whereas the latter is a centrally acting analgesic. Therefore their combination is expected to result in an additive or synergistic analgesia, thus allowing a decrease in the required doses of the individual agents, and consequently a reduced risk of adverse events.

2. Dexketoprofen and tramadol have different pharmacokinetic profiles, therefore their combination is expected to be characterised both by quick onset (typical of dexketoprofen) and long duration (peculiar to tramadol) of the analgesic effect.

However in the literature there are a wealth of examples concerning technical hurdles in producing adequate pharmaceutical preparations containing both ketoprofen and tramadol. For example, the common pharmaceutical excipient lactose monohydrate which is used in a variety of pharmaceutical compositions for oral use, e.g. tablets and film-coated tablets, leads to severe discoloration in tablets containing dexketoprofen, thus preventing its use.

Moreover, according to the literature, tramadol hydrochloride injection is found incompatible with acyclovir and clindamycin, while being stable when mixed with mannitol 20% or lactated Ringer's solution. Furthermore, as assessed for tramadol 50 mg/mL solution for injection or infusion, precipitation occurs when tramadol solution is mixed in the same syringe with solutions containing NSAIDs such as diclofenac sodium, indometacin and piroxicam.

In EP546676 a pharmaceutical composition comprising tramadol and a propionic acid derivative NSAID, which may be ketoprofen, is described, the preferred composition consisting of tramadol with ibuprofen. The compositions described in the examples are aqueous solutions and consequently no particular problems with solid compositions were noted.

WO2007008752 describes pharmaceutical compositions comprising two drugs which may be, among others, tramadol and a NSAID; the compositions are in a solid form, but the two drugs are in different layers for separate releases.

U.S. Pat. No. 6,294,195 discloses a sustained release oral analgesic dosage form for once-day administration comprising an opioid analgesic and optionally a non-opioid drug. Tramadol and ketoprofen are included, but shown examples are referred just to morphine.

WO2008/092219 discloses solid compositions with tramadol and ketoprofen. When mixing the solid ketoprofen and tramadol, an interaction between the two active ingredients is reported, as visualized by differential scanning calorimetry (DSC), resulting in a 'thick viscous mass hard to dissolve that could result in an alteration of the bioavailability of the drugs'. The patent application further describes different options to 'vehicle tramadol and ketoprofen in pharmaceutical forms and/or products that prevent any contact between them and/or impede interaction between the two active principles' assuming that the manufacturing following standard techniques and equipment is technically not feasible and will not lead to a stable pharmaceutical form. In this context, it should be noted that the intended field of treatment, namely moderate to severe pain, particularly demands the immediate-release of the active ingredients which might be hindered by the physical interaction of ketoprofen and tramadol.

Additionally, as described by Botha et al. (1989) in Drug Development and Industrial Pharmacy 15 (3), 415-426, Botha et al. (1990) in Drug Development and Industrial Pharmacy 16 (4), 673-683, Tita et al (2011) in Journal of Pharmaceutical and Biomedical Analysis, 56, 221-227, formulation development with ketoprofen and other NSAIDs such as naproxen is not trivial. Incompatibilities were detected for ketoprofen with common pharmaceutical filler materials such as lactose, calcium phosphates, magnesium stearate or Precirol Ato 5 (glyceryl palmitostearate), which might result in increase of disintegration time, impaired dissolution rates and decomposition during stability storage.

In addition, in AU703310B2 (EP7592963) 'A rapidly disintegrating medicinal form of tramadol or a tramadol salt', the preparation of binder-free tablets containing tramadol is described, since the development of binder-containing tablets with tramadol that show fast disintegration and dissolution is considered as not possible. In detail, it was outlined that tramadol hydrochloride closes the capillaries of a tablet during disintegration due to the high water solubility of this compound and leads to the rapid formation of a highly concentrated diffusion boundary layer. Moreover, the disintegration cannot be accelerated by increasing the content of disintegrating agent.

The unfavourable characteristics of tramadol in terms of drug product development become even more pronounced when it is combined with dexketoprofen. In fact, due to its sticky nature and the tendency to agglomerate, the latter should require the further processing in the form of binder-containing granules so precluding any binder-free tablets.

DESCRIPTION OF THE INVENTION

The drawbacks associated with the technology described in WO2008/092219 are overcome by the present invention, which provides the appropriate methodology to prepare pharmaceutically acceptable solid oral formulations of dexketoprofen and tramadol, both as salts, on the basis of standard techniques and equipment without the need of specialized procedures.

From the technological point of view, the basic principles for the manufacturing of these formulations, without the complex methodology which requires the separation of both active ingredients from each other, were identified and consist in:
- The active principles are both used as salts.
- The use of an appropriate filler material.
- The use of an appropriate binder system for the granulation, inducing a suitable granule size and granule structure.
- The use of an appropriate technology for the manufacturing, particularly in the case of the granulation procedures, i.e. by fluid bed granulation leading to a soft and easily disintegrating/dissolving granule structure which is especially suitable for a solid, immediate-release dosage form.

In order to avoid the potential physical incompatibility of dexketoprofen and tramadol and the formation of a hard and sticky mass as outlined in WO2008/092219, it is necessary to follow the established principles as described above and in the examples illustrated below. The combination of the identified parameters induces a stable and technologically feasible pharmaceutical dosage form suitable for the treatment of acute pain of moderate to severe intensity originated by different causes and related to different diseases such as: post-operative pain, headache, toothache, backpain, joint pain, inflammations and migraine.

According to WO2008/092219 the technological formulation of dexketoprofen and tramadol should necessitate the use of specialised, intricate techniques such as multi-layered tabletting, separate granulation of both active ingredients and/or the packaging in separate blister moldings in order to keep the two active ingredients rigorously separated. Surprisingly, however, the present invention shows that the manufacturing of a pharmaceutically stable formulation of these two active ingredients, suitable for the treatment of moderate to severe pain, is feasible without the application of non-standard methods and technologies. The present invention provides a technologically stable formulation containing the active principles dexketoprofen and tramadol together with excipients in pharmaceutically acceptable quality, in particular fillers and binders, wherein the filler is microcrystalline cellulose and the binder is preferably selected in the group of maize starch, pregelatinised maize starch, hypromellose or their mixtures.

For the purposes of the present invention hypromellose indicates hydroxypropylmethylcellulose or HPMC.

In a preferred embodiment, dexketoprofen is used as tromethamine (trometamol) salt and tramadol as the hydrochloride salt. Moreover, the production of the pharmaceutical dosage forms is performed with standard galenical processes such as mixing, sieving, granulating, tabletting and film-coating while applying standard technological equipment and machinery. Therefore, both active ingredients are not separated by specialized or unique manufacturing and or/packaging procedures such as tabletting in multi-layers, tabletting of two different granules/film-coated crystals or packaging in blisters with separated moldings.

According to the invention, dexketoprofen is in the form of a salt with organic or inorganic bases and tramadol as a salt with organic or inorganic acids.

The organic or inorganic base is selected from the group of trometamol, trimethylamine, dimethylamine, ethylamine, triethylamine, diethylamine, L-lysine, L-arginine, diethanolamine, sodium hydroxide, calcium hydroxide; the preferred being trometamol.

For the purposes of the present invention trometamol indicates 2-amino-2-hydroxymethyl-1,3-propanediol, also known as tromethamine or TRIS.

The organic or inorganic acid is selected from the group of hydrochloric, hydrobromic, phosphoric, sulfuric, methanesulfonic, benzenesulfonic, toluenesulfonic, acetic, propionic, malic, maleic, succinic, citric, L-tartaric, lactic, malonic, aspartic, glutamic; the preferred being hydrochloric.

The combination is directed to the treatment of acute and postoperative pain of moderate to severe intensity originated by different causes and related to different diseases selected from the group of headache, toothache, inflammations and migraine. The fixed combination of both compounds is intended to allow optimised pain control with fewer side effects than observed for both compounds alone.

According to the present invention the pharmaceutical forms comprise solid oral dosage forms, preferably immediate-release film-coated tablets.

According to the present invention, the pharmaceutical compositions contain a mixture of the two active ingredients, for oral dosage unit, in the following amount:
  Dexketoprofen (mol wt 254.28): between 8 and 50 mg, preferably between 10 and 30 mg, 12.5 mg and 25 mg being the most preferred amounts (equivalent to dexketoprofen trometamol (mol wt 375.42) between 11.8 and 73.8 mg, preferably between 14.8 and 44.3 mg, 18.4 mg and 36.9 mg being the most preferred specific amounts).

Tramadol (mol wt 263.28): between 17.6 and 105.4 mg, preferably between 26.3 and 87.8 mg, 32.9 mg and 65.9 mg being the most preferred specific amounts [equivalent to tramadol hydrochloride (mol wt 299.84) between 20 and 120 mg, preferably between 30 and 100 mg, 37.5 mg and 75 mg being the most preferred amounts].

The pharmaceutical compositions contain a mixture of the two active ingredients for oral dosage unit in a w/w ratio of dexketoprofen/tramadol between 2:1 to 1:10, preferably in a w/w ratio between 1:1 to 1:6 (equivalent to a w/w ratio of dexketoprofen trometamol/tramadol hydrochloride between 2.59:1 to 1:7.7, preferably 1.3:1 to 1:4.63).

The pharmaceutical compositions may contain in addition to the active ingredients one or more pharmaceutically acceptable excipients selected from pharmaceutical fillers, binders, disintegrants, lubricants and glidants.

The filler consists of microcrystalline cellulose and it should be contained in each dosage unit from 45% to 75% w/w of the total amount.

The binder, selected in the group consisting of maize starch, pregelatinised maize starch, hypromellose or mixtures thereof, in amounts from 5% to 20%, preferably from 7% to 12% by the total weight of the composition.

The disintegrant is selected from croscarmellose sodium and sodium starch glycolate or mixtures thereof, in amounts from 4% to 14% by the total composition weight.

The lubricant is selected in the group consisting of glycerol distearate, sodium stearyl fumarate or mixture thereof, sodium stearyl fumarate being the preferred one.

The preferred glidant is anhydrous colloidal silica.

According to the present invention, all the components of the compositions are intimately mixed. With the term intimately mixed a mixing of the components, and in particular of the two active principles, is intended in such a way that a physical contact among the components of the compositions, and in particular between the two active principles, is never precluded.

Oral dosage unit may optionally be coated with pharmaceutical excipients selected from pharmaceutical film formers, pigments, dispersants and polishing agents.

Dosage units are preferably coated with hypromellose or a poly(vinyl) alcohol based outer film coating.

Not all standard pharmaceutical excipients can be used together with dexketoprofen and tramadol. The use of lactose monohydrate which is a standard pharmaceutical excipient commonly used as filler material in combination with microcrystalline cellulose (e.g. MicroceLac) is not possible with dexketoprofen. The resulting tablets show yellow to orange stains indicating a chemical incompatibility and a significantly increased disintegration time after accelerated stability testing.

Also the use of the common binder polyvinylpyrrolidone (PVD) is precluded, as it leads to dull, porous tablet cores which are not suitable for further processing such as film coating, and to a strong increase in disintegration time and resistance to crushing.

Surprisingly pharmaceutical compositions containing i) a salt of dexketoprofen, trometamol being the preferred, ii) a salt of tramadol, hydrochloride being the preferred, iii) microcrystalline cellulose, as a filler, in high percentage w/w of the total amount, iv) a binder, v) one or more pharmaceutically acceptable excipients, wherein all the constituents are intimately mixed, result to be stable in all the studied conditions.

The pharmaceutical compositions can be manufactured following standard galenical processes in which both ingredients are not separated by specialized or unique manufacturing and/or packaging procedures; they can be manufactured by fluid bed granulation or fluid bed drying in tablets or capsules for the immediate-release of both active principles.

The compositions prepared according to the present invention show a dissolution of the two active ingredients, dexketoprofen and tramadol, in a time range not superior to 15 minutes, more precisely between 3 and 11 minutes.

The compositions show a dissolution rate and a purity profile of the components which remain un-changed during shelf-life of 18 months at (25±2°) C. and (60±5)% relative humidity in aluminium-aluminium and PVC/PVDC-aluminium blisters.

EXPERIMENTAL SECTION

Dexketoprofen shows a pronounced physicochemical incompatibility with tramadol. This interaction is elucidated below (Example A).

Example A: Compatibility Testing of Dexketoprofen Trometamol and Tramadol Hydrochloride as Dry Powder Mixtures Dexketoprofen trometamol and tramadol hydrochloride were mixed together at different ratios and subjected to accelerated conditions, i.e. (60+/−2°) C. and 60% relative humidity. The corresponding results are presented in table A1.

TABLE A

Appearance of dry powder mixtures containing dexketoprofen and tramadol

| Composition | Results (after weeks) | | | |
|---|---|---|---|---|
| | 0 | 1 | 2 | 4 |
| Dexketoprofen trometamol (DKP TRIS) | n.t. | n.t. | loose powder | agglomerated powder |
| Tramadol hydrochloride (TRA-HCl) | n.t. | n.t. | loose powder | slightly agglutinated powder |
| DKP TRIS + TRA-HCl (25 mg + 37.5 mg) | n.t. | loose powder | n.t. | agglomerated powder |
| DKP TRIS + TRA-HCl (12.5 mg + 75 mg) | n.t. | hard and agglutinated mass at the bottom of the vial | n.t. | hard and agglutinated mass at the bottom of the vial | n.t. = not tested

These results demonstrate the physical interaction between dexketoprofen trometamol and tramadol hydrochloride drug substances, especially in the case of high tramadol doses (e.g. 75 or 100 mg).

The result obtained in EXAMPLE A makes it unlikely for the person skilled in the art to define an effective and stable pharmaceutical composition of both components in the form of a binder-containing tablet. As shown in the following EXAMPLES 1 to 4 of the present invention, however, the selection of the right components applied in the correct ratio and processed in the appropriate manufacturing procedures decide about the functionality and stability of drug product. The comparative EXAMPLES B and C are provided to illustrate this finding.

Example B: Selection of the Appropriate Binder System for Dexketoprofen+Tramadol Tablets For the definition of the appropriate binder system of dexketoprofen+tramadol drug product, conventional pharmaceutical binders such as polyvinylpyrrolidone, hypromellose and pregelatinized maize starch were evaluated.

The tablets were manufactured in accordance with the composition presented in table B.

TABLE B

Composition of tablet cores used for the screening of the appropriate binder system

| | | | Quantity, mg per tablet | | | |
|---|---|---|---|---|---|---|
| Ingredient | Reference | Function | 1 | 2 | 3 | 4 |
| Dexketoprofen trometamol (equivalent to dexketoprofen) | Manufacturers specification | Active ingredient | 36.90 (25.0) | 36.90 (25.0) | 36.90 (25.0) | 36.90 (25.0) |
| Tramadol hydrochloride | Ph. Eur. | Active ingredient | 75.00 | 75.00 | 75.00 | 75.00 |
| Microcrystalline cellulose | Ph. Eur. | Filler | 239.10 | 276.54 | 299.94 | 309.30 |
| Polyvinylpyrrolidone | Ph. Eur. | Binder | 84.24 | — | — | — |
| Maize starch, pregelatinized | Ph. Eur. | Binder | — | 46.80 | — | — |
| Hypromellose | Ph. Eur. | Binder | — | — | 23.40 | 14.04 |
| Croscarmellose sodium | Ph. Eur. | Disintegrant | 18.72 | 18.72 | 18.72 | 18.72 |
| Glycerol distearate | Ph. Eur. | Lubricant | 9.36 | 9.36 | 9.36 | 9.36 |
| Silica colloidal, anhydrous | Ph. Eur. | Glidant | 4.68 | 4.68 | 4.68 | 4.68 |
| Purified water* | Ph. Eur. | Solvent for granulation | q.s. | q.s. | q.s. | q.s. |
| Total tablet core weight | | | 468.00 | 468.00 | 468.00 | 468.00 |

1 = binder system polyvinylpyrrolidone
2 = binder system pregelatinized maize starch,
3 = binder system hypromellose 5% w/w
4 = binder system hypromellose 3% w/w The amount of polyvinylpyrrolidone was selected in accordance with previous experiences leading to a favourable particle size and granule properties. All the mixtures were sieved, granulated and subjected to tablet compaction. The appearance of the resulting tablet cores is presented in table C.

TABLE C

Appearance of tablet cores manufactured with different binder systems

| | Formulation | | | |
|---|---|---|---|---|
| Parameter | 1 | 2 | 3 | 4 |
| Appearance of the tablet cores | dull, slightly porous | shiny, brilliant | dull, dark-spotted | slightly shining | n.t. = not tested

Subsequently, the tablet cores were subjected to accelerated stability testing at 60° C. and tested for disintegration time and tablet hardness (tables E and F).

TABLE D

Disintegration time of dexketoprofen + tramadol formulations in tablets with different binder systems

| | Disintegration time [min.] after weeks at 60° C. | | |
|---|---|---|---|
| Formulation | 0 | 2 | 4 |
| 1 (polyvinyl-pyrrolidone) | 3 | 16 | 17 |
| 2 (maize starch pregelatinized) | 2 | 7 | 10 |

TABLE D-continued

Disintegration time of dexketoprofen + tramadol formulations in tablets with different binder systems

| | Disintegration time [min.] after weeks at 60° C. | | |
|---|---|---|---|
| Formulation | 0 | 2 | 4 |
| 3 (hypromellose 5% w/w) | 3 | 8 | 8 |
| 4 (hypromellose 3% w/w) | 2 | 6 | 4 |

TABLE E

Resistance to crushing of dexketoprofen + tramadol formulations in tablets with different binder systems

| | Resistance to crushing [N] after weeks at 60° C. | | |
|---|---|---|---|
| Formulation | 0 | 2 | 4 |
| 1 (polyvinyl-pyrrolidone) | 90 | 123 | 123 |
| 2 (maize starch pregelatinized) | 134 | 127 | 116 |
| 3 (hypromellose 5% w/w) | 128 | 120 | 119 |
| 4 (hypromellose 3% w/w) | 165 | 126 | 122 |

The obtained results from binder screening underline that the number of suitable binders for dexketoprofen+tramadol containing tablets is limited. The use of the standard binder polyvinylpyrrolidone is precluded, as it leads to dull, porous tablet cores which are not suitable for further processing such as film coating, and to a strong increase of disintegration time and resistance to crushing. The increase of disintegration time was also detected for tablet cores formulated on the basis of pregelatinized maize starch and hypromellose 3% w/w and 5% w/w, but to a far lesser extent and without the increase of tablet hardness. Therefore, any binder system containing the commonly used polyvinylpyrrolidone does not alleviate the incompatibility of dexketoprofen and tramadol, but rather seems to support the negative effects of this interaction. After storage at accelerated conditions, the obtained tablet cores are no longer compliant with the requirements of Ph. Eur., i.e. disintegration time below 15 minutes.

EXAMPLE C illustrates the possible option to overcome the observed increase in disintegration time in tablet cores with maize starch, pregelatinized, by the application of an appropriate lubricant system.

Example C: Selection of the Appropriate Lubricant in Combination with Appropriate Binder System In order to diminish the observed increase in disintegration time over shelf-life, different types of lubricant were tested in tablet cores formulated with maize starch pregelatinized. As magnesium stearate was described in literature to be incompatible with (dex)ketoprofen (2) and naproxen (3), this excipient was excluded, so that the study was conducted with glycerol distearate and sodium stearyl fumarate. The corresponding formulations and results are summarized in tables F and G.

TABLE F

Composition of tablet cores used for the lubricant screening

| Ingredient | Reference | Function | Quantity, mg per tablet 1 | 2 |
|---|---|---|---|---|
| Dexketoprofen trometamol (equivalent to dexketoprofen) | Manufacturers specification | Active ingredient | 36.90 (25.0) | 36.90 (25.0) |
| Tramadol hydrochloride | Ph. Eur. | Active ingredient | 75.00 | 75.00 |
| Microcrystalline cellulose | Ph. Eur. | Filler | 253.14 | 253.14 |
| Maize starch, pregelatinized | Ph. Eur. | Binder | 46.80 | 46.80 |
| Croscarmellose sodium | Ph. Eur. | Disintegrant | 46.80 | 18.72 |
| Glycerol distearate | Ph. Eur. | Lubricant | 4.68 | — |
| Sodium stearyl fumarate | Ph. Eur. | Lubricant | — | 4.68 |
| Silica colloidal, anhydrous | Ph. Eur. | Glidant | 4.68 | 4.68 |
| Purified water* | Ph. Eur. | Solvent for granulation | q.s. | q.s. |
| Total tablet core weight | | | 468.00 | 468.00 |

TABLE G

Disintegration time of dexketoprofen + tramadol formulations in tablets with different types of lubricant

| | Disintegration time [min.] after weeks at 60° C. | | |
|---|---|---|---|
| Formulation | 0 | 1 | 4 |
| 1 (glycerol distearate) | 2 | 4 | 5 |
| 2 (sodium stearyl fumarate) | 3 | 2 | 3 |

The disintegration time of tablet cores prepared with 1% w/w glycerol distearate significantly increased from 2 min. to 4 min. after 1 week and to 5 min. after 4 weeks at 60° C. In contrast, tablet cores with identical parameters and identical formulation except for the use of 1% sodium stearyl fumarate instead of glycerol distearate showed no increase at all in the disintegration time (3 min. at point zero vs. 2 min. after 1 week and vs. 3 min after 4 weeks at 60° C.).

In summary, the experimental EXAMPLES A to C indicate that the formulation development for dexketoprofen+ tramadol tablets requires specific strategies and that the number of potential excipients that are appropriate is limited.

BRIEF DESCRIPTION OF THE DRAWINGS

FIG. 1: Dissolution profile of active ingredients, initial conditions.

FIG. 2: Dissolution profile of active ingredients after 1 week at 60° C.

FIG. 3: Dissolution profile of active ingredients after 4 weeks at 60° C.

FIG. 4: Dissolution profile of film-coated tablets (pilot batch), initial conditions.

FIG. 5: Dissolution profile of film-coated tablets (100 kg manufactured sub-batch), initial conditions.

EXAMPLES

The examples comprise solid oral dosage forms in several combinations. However, the dosage strengths which can be prepared with the present invention are not limited to these combinations only.

The detailed description of the examples is intended to illustrate the invention, but not to limit its scope.

Example 1: Manufacturing of Dexketoprofen Trometamol+Tramadol Hydrochloride Tablet or Film-Coated Tablets, with Maize Starch Batch size: 4 kg The composition and batch formulas of the (film-coated) tablets with the combination dosage strengths DKP TRIS 18.4 mg+TRA-HCl 37.5 mg (1), DKP TRIS 18.4 mg+TRA-HCl 75 mg (2), DKP TRIS 36.9 mg+TRA-HCl 37.5 mg (3) and DKP TRIS 36.9 mg+TRA-HCl 75 mg (4) are given in table 1 and table 2, respectively.

TABLE 1

Composition of the tablets and film-coated tablets, respectively:

| Ingredient | Reference | Function | Quantity, mg per tablet | | | |
| --- | --- | --- | --- | --- | --- | --- |
| | | | 1 | 2 | 3 | 4 |
| Tablet core | | | | | | |
| Dexketoprofen trometamol (equivalent to dexketoprofen) | Manufacturers specification | Active ingredient | 18.45 (12.5) | 18.45 (12.5) | 36.90 (25.0) | 36.90 (25.0) |
| Tramadol hydrochloride | Ph. Eur. | Active ingredient | 37.50 | 75.00 | 37.50 | 75.00 |
| Microcrystalline cellulose | Ph. Eur. | Filler | 378.85 | 341.35 | 360.40 | 322.90 |
| Maize starch | Ph. Eur. | Binder | 49.60 | 49.60 | 49.60 | 49.60 |
| Sodium starch glycolate | Ph. Eur. | Disintegrant | 27.10 | 27.10 | 27.10 | 27.10 |
| Glycerol distearate | Ph. Eur. | Lubricant | 5.20 | 5.20 | 5.20 | 5.20 |
| Silica colloidal, anhydrous | Ph. Eur. | Glidant | 3.30 | 3.30 | 3.30 | 3.30 |
| Purified water* | Ph. Eur. | Solvent for granulation | q.s. | q.s. | q.s. | q.s. |
| Total tablet core weight | | | 520.00 | 520.00 | 520.00 | 520.00 |
| Film-coating (optional) | | | | | | |
| Hypromellose | Ph. Eur. | Film former | 4.95 | 4.95 | 4.95 | 4.95 |
| Titanium dioxide | Ph. Eur. | Pigment | 3.24 | 3.24 | 3.24 | 3.24 |
| Povidone K 30 | Ph. Eur. | Dispersant | 0.87 | 0.87 | 0.87 | 0.87 |
| Macrogol 4000 | Ph. Eur. | Polishing agent | 0.95 | 0.95 | 0.95 | 0.95 |
| Purified water* | Ph. Eur. | Solvent for film-coating | q.s. | q.s. | q.s. | q.s. |
| Total weight of film coated tablet | | | 530.01 | 530.01 | 530.01 | 530.01 |

*not part of the final drug product

TABLE 2

Batch formulas of the tablets and film-coated tablets, respectively:

| Ingredient | Reference | Quantity, g per batch | | | |
| --- | --- | --- | --- | --- | --- |
| | | 1 | 2 | 3 | 4 |
| Tablet core | | | | | |
| Dexketoprofen trometamol | Manufacturers specification | 141.923 | 141.923 | 283.846 | 283.846 |
| Tramadol hydrochloride | Ph. Eur. | 288.462 | 576.923 | 288.462 | 576.923 |
| Microcrystalline cellulose | Ph. Eur. | 2914.231 | 2625.769 | 2772.308 | 2483.846 |

TABLE 2-continued

Batch formulas of the tablets and film-coated tablets, respectively:

| Ingredient | Reference | Quantity, g per batch | | | |
|---|---|---|---|---|---|
| | | 1 | 2 | 3 | 4 |
| Maize starch | Ph. Eur. | 381.538 | 381.538 | 381.538 | 381.538 |
| Sodium starch glycolate | Ph. Eur. | 208.462 | 208.462 | 208.462 | 208.462 |
| Glycerol distearate | Ph. Eur. | 40.000 | 40.000 | 40.000 | 40.000 |
| Silica colloidal, anhydrous | Ph. Eur. | 25.385 | 25.385 | 25.385 | 25.385 |
| Purified water (solvent for granulation) * | Ph. Eur. | q.s. | q.s. | q.s. | q.s. |
| Film coating (optional) | | | | | |
| Hypromellose | Ph. Eur. | 38.077 | 38.077 | 38.077 | 38.077 |
| Titanium dioxide | Ph. Eur. | 24.923 | 24.923 | 24.923 | 24.923 |
| Povidone K 30 | Ph. Eur. | 6.692 | 6.692 | 6.692 | 6.692 |
| Macrogol 4000 | Ph. Eur. | 7.308 | 7.308 | 7.308 | 7.308 |
| Purified water (solvent for film coating)* | Ph. Eur. | q.s. | q.s. | q.s. | q.s. |

Dexketoprofen trometamol and tramadol hydrochloride are sieved together with microcrystalline cellulose and about ½ of maize starch through 1.0 mm mesh size. The compounds are mixed for 20 min. With the remaining amount of maize starch the granulation fluid is prepared: approximately ⅓ of water is mixed with the second half of maize starch. The remaining water is heated to near the boiling point and then added to the maize starch slurry. For the wet granulation the binder fluid is stirred to 72-80° C. The granulation is performed applying standard procedures using a fluid bed granulator. It is dried to a loss on drying of 2.5-3.5%. Afterwards, the granules are sieved (1.0 mm mesh size) and subsequently mixed with sodium starch glycolate, glycerol distearate and silica colloidal anhydrous for 10 min. The obtained compactable mixture is compressed on a standard rotary die press to tablet cores with the following properties:

Oblong with dimensions of 17×8 mm
Tablet mass: 520±3%
Height: 5.5±0 2 mm
Resistance to crushing: ≥90 N
Disintegration time: ≤5 min.
Friability: ≤1.0%

The resulting tablet cores can be coated with the hypromellose film. The hypromellose is added to purified water heated to near the boiling point. Afterwards, povidone K 30 and macrogol 4000 are added and the mixture is stirred until a clear solution is obtained. Directly before the film-coating, titanium dioxide is added and dispersed with a high frequency stirrer. The film-coating is performed in a standard film-coater.

The obtained film-coated tablets show the following properties:

Tablet mass: 530±5%
Height: 5.6±0 3 mm
Resistance to crushing: ≥90 N
Disintegration time: ≤7.5 min.

Sample batches with different dexketoprofen/tramadol ratios were produced and tested under ICH conditions for 18 months at (25±2°) C. and (60±5)% relative humidity. Results of these tests are presented in tables 3 to 6.

The obtained results indicate excellent chemical and physical stability of the produced batches (regarding disintegration, dissolution and other tablet parameters).

TABLE 3

Stability data of the film-coated tablets DKP TRIS 18.4 mg + TRA-HCl 37.5 mg at (25 ± 2)° C. and (60 ± 5)% RH in Al—Al blisters:

| Test parameters | Shelf-life specification | Results (after months) | | | | | |
|---|---|---|---|---|---|---|---|
| | | 0 | 3 | 6 | 9 | 12 | 18 |
| General and specific characteristics of the dosage form | | | | | | | |
| Dissolution (after 30 min) | | | | | | | |
| Dexketoprofen TRIS [%] | (Q = 75) | 101 | 98 | 99 | 100 | 101 | 101 |
| Tramadol hydrochloride [%] | (Q = 75) | 102 | 102 | 101 | 102 | 102 | 102 |
| Disintegration time [min] | nmt 15 | 3 | 4 | 5 | 4 | 3 | 4 |
| Assay | | | | | | | |
| Dexketoprofen TRIS [%] | 90.0 to 105.0 | 99.4 | 102.1 | 100.2 | 100.7 | 100.4 | 102.2 |
| Tramadol hydrochloride [%] | 90.0 to 105.0 | 99.7 | 101.8 | 102.9 | 102.0 | 101.6 | 105.0 |
| Additional parameter | | | | | | | |
| Resistance to crushing mean | t: ≥90N | 203 | 252 | 198 | 189 | 189 | 199 | nmt = not more than

TABLE 4

Stability data of the film-coated tablets DKP TRIS 18.4 mg + TRA-HCl 75 mg at (25 ± 2)° C. and (60 ± 5)% RH in Al—Al blisters:

| Test parameters | Shelf-life specification | \multicolumn{6}{c}{Results (after months)} | | | | | |
|---|---|---|---|---|---|---|---|
| | | 0 | 3 | 6 | 9 | 12 | 18 |
| General and specific characteristics of the dosage form Dissolution (after 30 min) | | | | | | | |
| Dexketoprofen TRIS [%] | (Q = 75) | 102 | 100 | 101 | 101 | 98 | 102 |
| Tramadol hydrochloride [%] | (Q = 75) | 103 | 100 | 102 | 100 | 100 | 102 |
| Disintegration time [min] | nmt 15 | 6 | 7 | 9 | 9 | 11 | 8 |
| Assay | | | | | | | |
| Dexketoprofen TRIS [%] | 90.0 to 105.0 | 99.1 | 101.7 | 101.3 | 103.3 | 100.9 | 101.6 |
| Tramadol hydrochloride [%] | 90.0 to 105.0 | 99.2 | 101.8 | 101.3 | 103.1 | 101.1 | 101.2 |
| Additional parameter | | | | | | | |
| Resistance to crushing mean | t: ≥90N | 200 | 224 | 189 | 194 | 183 | 192 | nmt = not more than

TABLE 5

Stability data of the film-coated tablets DKP TRIS 36.9 mg + TRA-HCl 37.5 mg at (25 ± 2)° C. and (60 ± 5)% RH in Al—Al blisters:

| Test parameters | Shelf-life specification | \multicolumn{6}{c}{Results (after months)} | | | | | |
|---|---|---|---|---|---|---|---|
| | | 0 | 3 | 6 | 9 | 12 | 18 |
| General and specific characteristics of the dosage form Dissolution (after 30 min) | | | | | | | |
| Dexketoprofen TRIS [%] | (Q = 75) | 102 | 101 | 102 | 100 | 101 | 102 |
| Tramadol hydrochloride [%] | (Q = 75) | 101 | 100 | 100 | 100 | 100 | 101 |
| Disintegration time [min] | nmt 15 | 3 | 5 | 6 | 3 | 1 | 3 |
| Assay | | | | | | | |
| Dexketoprofen TRIS [%] | 90.0 to 105.0 | 98.2 | 102.3 | 101.6 | 102.2 | 101.1 | 102.4 |
| Tramadol hydrochloride [%] | 90.0 to 105.0 | 96.8 | 100.5 | 101.4 | 100.8 | 98.7 | 101.4 |
| Additional parameter | | | | | | | |
| Resistance to crushing mean | t: ≥90N | 207 | 257 | 190 | 205 | 203 | 204 | nmt = not more than

TABLE 6

Stability data of the film-coated tablets DKP TRIS 36.9 mg + TRA-HCl 75 mg at (25 ± 2)° C. and (60 ± 5)% RH in Al—Al blisters:

| Test parameters | Shelf-life specification | \multicolumn{6}{c}{Results (after months)} | | | | | |
|---|---|---|---|---|---|---|---|
| | | 0 | 3 | 6 | 9 | 12 | 18 |
| General and specific characteristics of the dosage form Dissolution (after 30 min) | | | | | | | |
| Dexketoprofen TRIS [%] | (Q = 75) | 104 | 103 | 103 | n.t. | 101 | 99 |
| Tramadol hydrochloride [%] | (Q = 75) [1] | 104 | 101 | 102 | n.t. | 103 | 99 |
| Disintegration time [min] | nmt 15 | 3 | 8 | 9 | 8 | 7 | 8 |
| Assay | | | | | | | |
| Dexketoprofen TRIS [%] | 90.0 to 105.0 | 100.5 | 103.1 | 103.0 | 103.2 | 104.9 | 104.1 |
| Tramadol hydrochloride [%] | 90.0 to 105.0 | 100.6 | 102.4 | 103.1 | 103.4 | 102.7 | 102.6 |
| Additional parameter | | | | | | | |
| Resistance to crushing mean | t: ≥90N | 152 | 184 | 170 | 167 | 174 | 183 | nmt = not more than

Example 2: Manufacturing of Dexketoprofen Trometamol+Tramadol Hydrochloride Film-Coated Tablets with Pregelatinised Maize Starch Batch size: 550 g
Composition of the film-coated tablets:

| Active substances | Amount per single dose unit [mg] | Amount per batch [g] |
|---|---|---|
| Dexketoprofen trometamol | 36.90 | 57.99 |
| Tramadol hydrochloride | 75.00 | 117.86 |
| Other ingredients | | |
| Tablet core: | | |
| Microcrystalline cellulose | 179.70 | 282.39 |
| Maize starch pregelatinised | 29.20 | 45.89 |
| Croscarmellose sodium | 21.90 | 34.41 |
| Sodium stearyl fumarate | 3.65 | 5.74 |
| Silica, colloidal anhydrous | 3.65 | 5.74 |
| Purified water* | q.s. | q.s. |
| Film coating: | | |
| polyvinyl alcohol based coating | 7.30 | 11.47 |
| Purified water* | q.s. | q.s. |

*not part of the final product

Dexketoprofen trometamol and tramadol hydrochloride are sieved together with microcrystalline cellulose and ½ of croscarmellose sodium through 1.0 mm mesh size. The compounds are transferred to the fluid bed granulator. For the preparation of the binder fluid pregelatinised maize starch is added to purified water and stirred for about 60 min. in order to obtain homogenous binder slurry. The granulation is performed applying standard procedures in a fluid bed granulator. It is dried to a loss on drying of 2.5-3.5%.

Afterwards, the granules are sieved (1.0 mm mesh size) and subsequently mixed with croscarmellose-sodium, silica, colloidal anhydrous for 10 min. After the mixture with sodium stearyl fumarate for 5 min., the obtained compactable mixture is compressed on a standard rotary tablet press to tablet cores with the following properties:

Oblong with dimensions of 16×7 mm

Tablet mass: 350 mg±5%

Height: 4.5±0 2 mm

Resistance to crushing: ≥90 N

Disintegration time: ≤4 min.

Friability: ≤1.0%

The resulting tablet cores are subsequently coated with an aqueous film coating system based on a polyvinyl alcohol motif, which is prepared according to the manufacturer's recommendation. The film-coating is performed in a standard film-coater. The resulting film-coated tablets show the following properties:

Tablet mass: 357 mg±5%

Height: 4.6±0 2 mm

Resistance to crushing: ≥90 N

Disintegration time: ≤6 min.

Figure 1:
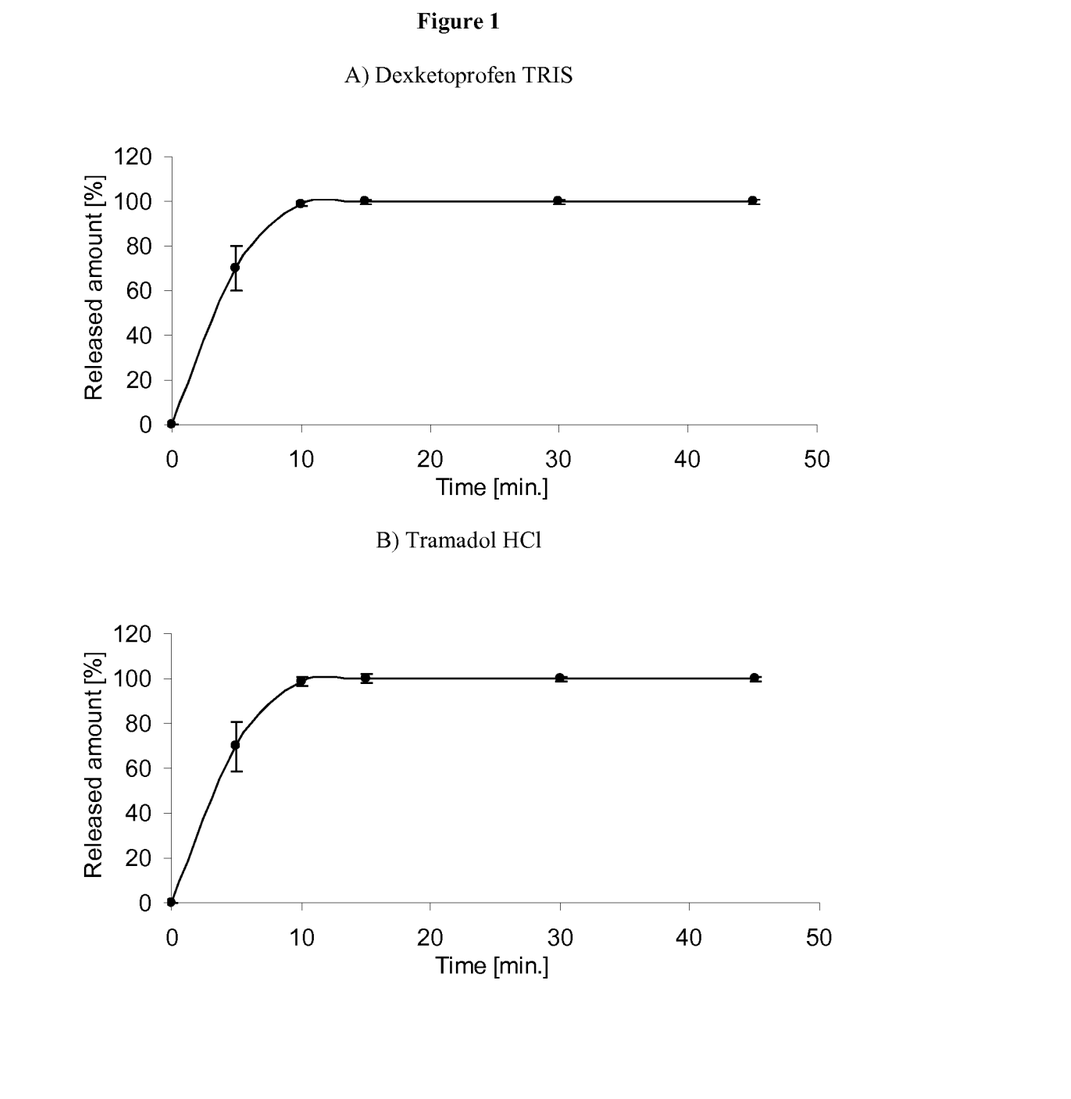
FIGS. 1, 2 and 3 are graphs showing the dissolution behaviour of both active ingredients, dexketoprofen TRIS and tramadol hydrochloride, respectively at the initial conditions and after accelerated stability tests (1 and 4 weeks at 60° C.). The dissolution tests were performed, according to USP, in pH 6.8 R1 buffer, using a paddle apparatus, at a speed of 50 rpm and in a volume of 1000 ml.
Figure 2:
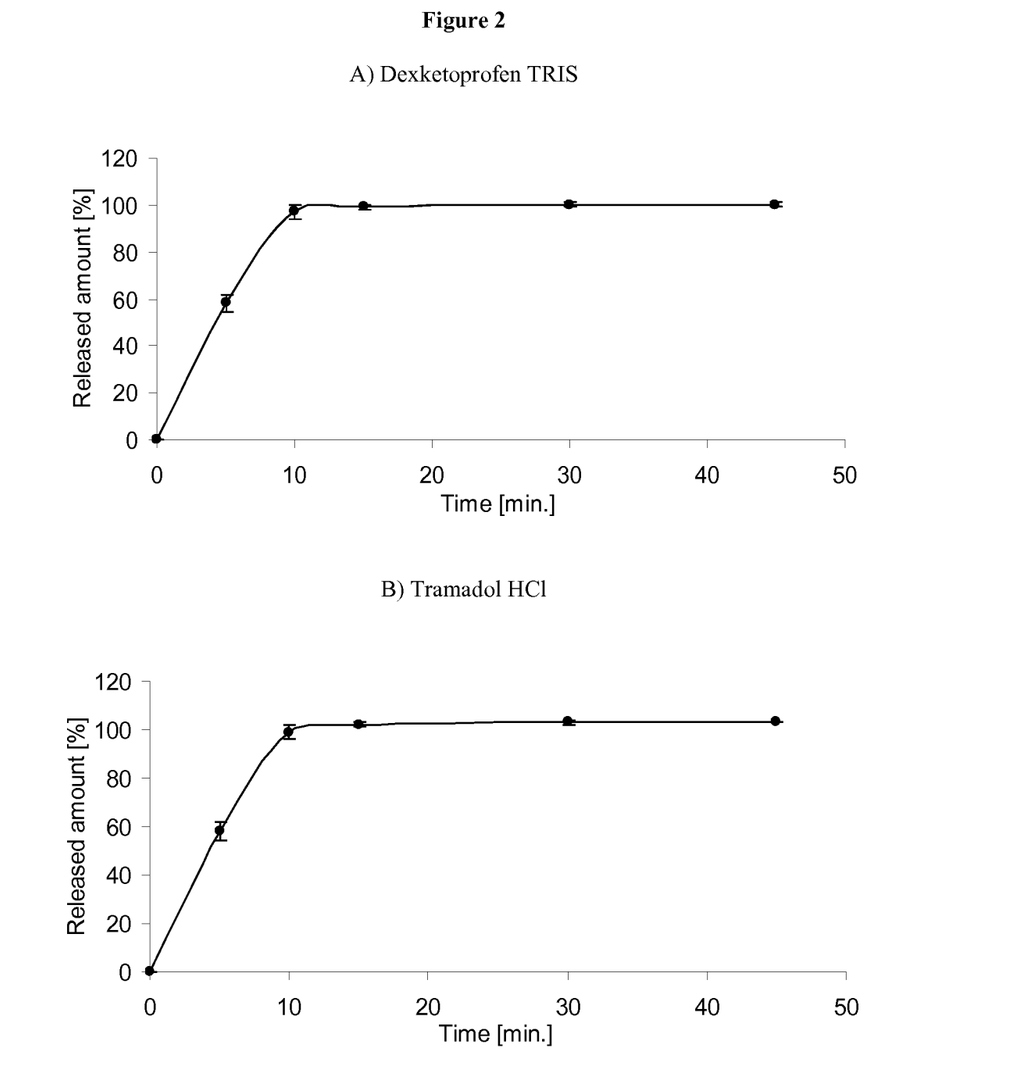
Figure 3:
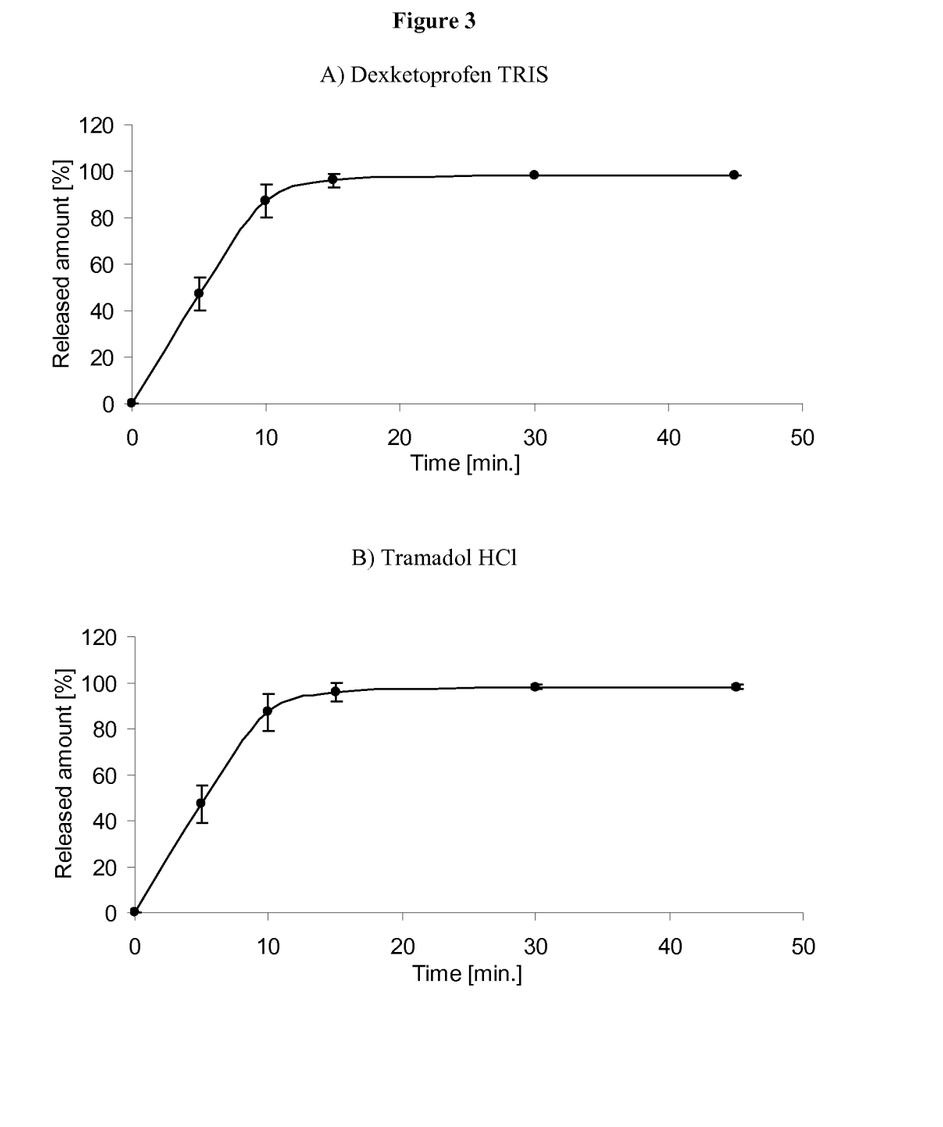

The dissolution profiles of the film-coated tablets in Ph. Eur. buffer pH 6.8 R1 with paddle apparatus, at 50 rpm of stirring speed and 1000 ml of buffer volume are shown in FIGS. 1, 2 and 3. FIG. 1 presents the dissolution profiles of both active ingredients at the initial value, whereas FIGS. 2 and 3 displays the dissolution profiles after accelerated stability testing for 1 and 4 weeks, respectively, at 60° C. in a dry oven. No significant difference between the dissolution profiles was detectable, so that a physico-chemical interaction of both compounds can be excluded.

Example 3: Manufacturing of Dexketoprofen+Tramadol Film-Coated Tablets with Pregelatinised Maize Starch as Binder and Croscarmellose Sodium as Disintegrant in Pilot Batch Scale (12.7 kg)

The identical formulation as presented in EXAMPLE 2 was upscaled to 12.7 kg (pilot scale). The characteristics for the tablet cores are presented below:

Oblong with dimensions of 14×6 mm

Tablet mass: 350 mg±5%

Height: 5.1±0 5 mm

Resistance to crushing: 130±15 N

Disintegration time: ≤6 min.

Friability: ≤0.5%

The properties of the film-coated tablets are as follows:

Tablet mass: 357 mg±5%

Height: 5.2±0 5 mm

Resistance to crushing: ≥90 N

Disintegration time: ≤15 min.

Figure 4:
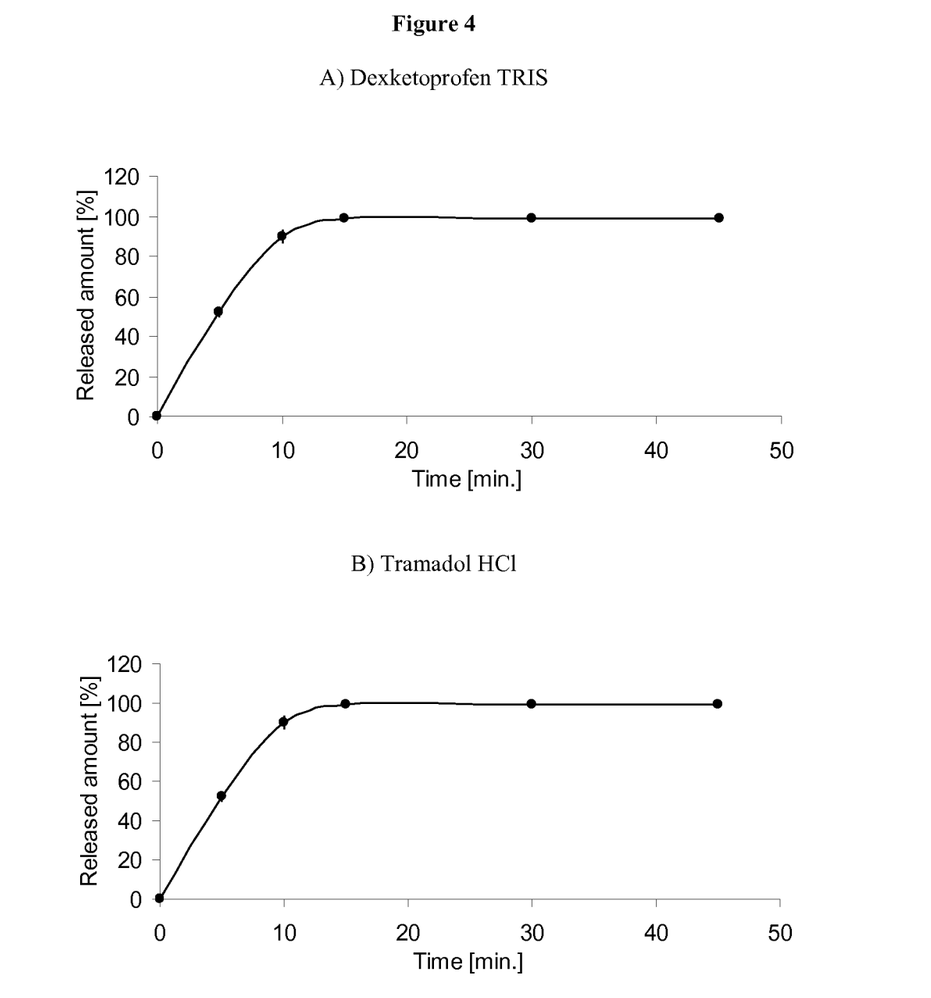
FIG. 4: shows the dissolution profile of the film-coated tablets of dexketoprofen TRIS and tramadol hydrochloride derived from a pilot batch production, at the initial conditions.

The film-coated tablets were tested for the dissolution profile and for stability under accelerated conditions at 40° C./75% relative humidity. The results are presented in FIG. 4 and table 7.

TABLE 7

Stability data of the film-coated tablets DKP TRIS 36.9 mg + TRA-HCl 75 mg at (25 ± 2)° C. and (60 ± 5)% RH in A1-A1 blisters

| Test parameters | Shelf-life specification | Results (after months) | | |
|---|---|---|---|---|
| | | 0 | 3 | 6 |
| General and specific characteristics of the dosage form Dissolution (after 30 min) | | | | |
| Dexketoprofen TRIS [%] | (Q = 75) [1] | 98 | 101 | 98 |
| Tramadol hydrochloride [%] | (Q = 75) [1] | 99 | 102 | 99 |
| Disintegration time [min] | nmt 15 | 6 | 7 | 6 |
| Assay | | | | |
| Dexketoprofen TRIS [%] | 90.0 to 105.0 | 101.3 | 99.6 | 99.2 |
| Tramadol hydrochloride [%] | 90.0 to 105.0 | 102.7 | 101.4 | 100.8 |
| Additional parameter | | | | |
| Resistance to crushing [N] [7] | t: ≥90 | 191 | 228 | 233 |

Example 4: Manufacturing of Dexketoprofen+Tramadol Film-Coated Tablets with Pregelatinised Maize Starch as Binder and Croscarmellose Sodium as Disintegrant in the Large Scale of 223 kg The formulation from EXAMPLES 2 and 3 was slightly modified and upscaled to the large-scale batch size of 223 kg. The granulation was performed in two sub-batches. Composition of the Film-Coated Tablets:

| Active substances | Amount per single dose unit [mg] | Amount per granulation sub-batch [kg] | Amount per batch [kg] |
|---|---|---|---|
| Dexketoprofen trometamol | 36.90 | 11.121 | 22.241 |
| Tramadol hydrochloride | 75.00 | 22.603 | 45.206 |
| Other ingredients Tablet core: | | | |
| Microcrystalline cellulose | 179.70 | 54.157 | 108.314 |
| Maize starch pregelatinised | 29.20 | 8.800 | 17.600 |
| Croscarmellose sodium (inner phase) | 11.02 | 3.321 | 6.642 |
| Croscarmellose sodium (outer phase) | 22.04 | — | 13.292 |
| Sodium stearyl fumarate | 1.83 | — | 4.442 |
| Silica, colloidal anhydrous | 7.37 | — | 1.103 |
| Purified water* | q.s. | — | |
| Film coating: | | | |
| polyvinyl alcohol based coating | 7.30 | — | 4.400 |
| Purified water* | q.s. | — | q.s. |

For the first sub-batch of 100 kg, dexketoprofen trometamol, tramadol hydrochloride, microcrystalline cellulose and croscarmellose-sodium for the inner phase mixed and sieved together through 1.0 mm mesh size. The compounds are transferred to the fluid bed granulator. For the preparation of the binder fluid pregelatinised maize starch is added to purified water and stirred for about 60 min. in order to obtain a homogenous binder slurry. The granulation is performed applying standard procedures in a fluid bed granulator. It is dried to a loss on drying of 2.5-3.5%. Afterwards, the granules are sieved (1.0 mm mesh size) and subsequently mixed with croscarmellose-sodium and silica, colloidal anhydrous for 10 min. The second sub-batch is prepared following identical procedures and then added to the first sub-batch. Sodium stearyl fumarate is sieved and added to the mixture of both sub-batches. The obtained compactable mixture is compressed on a standard rotary tablet press to tablet cores with the following properties:

Oblong with dimensions of 14×6 mm
Tablet mass: 363 mg±2%
Height: 5.1±0 2 mm
Resistance to crushing: 115-150 N
Disintegration time: <5 min.
Friability: ≤0.05%

The properties of the film-coated tablets are as follows:
Tablet mass: 370 mg±5%
Height: 5.2±0.2 mm
Resistance to crushing: >90 N
Disintegration time: ≤6 min.

TABLE 8

Stability data of the film-coated tablets DKP TRIS 36.9 mg + TRA-HCl 75mg at (40 ± 2)° C. and (75 ± 5)% RH in A1-A1 blisters

| Test parameters | Shelf-life specification | Results (after months) | | |
|---|---|---|---|---|
| | | 0 | 3 | 6 |
| General and specific characteristics of the dosage form | | | | |
| Dissolution (after 30 min) | | | | |
| Dexketoprofen TRIS [%] | (Q = 75) | 100 | 98 | 98 |
| Tramadol hydrochloride [%] | (Q = 75) | 100 | 98 | 100 |
| Disintegration time [min] | nmt 15 | 8 | 8 | 9 |
| Assay | | | | |
| Dexketoprofen TRIS [%] | 90.0 to 105.0 | 98.7 | 99.5 | 98.8 |
| Tramadol hydrochloride [%] | 90.0 to 105.0 | 100.5 | 100.1 | 100.0 |
| Additional parameter | | | | |
| Resistance to crushing [N] | t: ≥90 | 221 | 255 | 266 |

TABLE 9

Stability data of the film-coated tablets DKP TRIS 36.9 mg + TRA-HCl 75 mg at (30 ± 2)° C. and (75 ± 5)% RH in A1-A1 blisters

| Test parameters | Shelf-life specification | Results (after months) | | |
|---|---|---|---|---|
| | | 0 | 3 | 6 |
| General and specific characteristics of the dosage form | | | | |
| Dissolution (after 30 min) | | | | |
| Dexketoprofen TRIS [%] | (Q = 75) | 100 | 94 | 96 |
| Tramadol hydrochloride [%] | (Q = 75) | 100 | 95 | 95 |
| Disintegration time [min] | nmt 15 | 8 | 8 | 8 |
| Assay | | | | |
| Dexketoprofen TRIS [%] | 90.0 to 105.0 | 98.7 | 100.1 | 97.6 |
| Tramadol hydrochloride [%] | 90.0 to 105.0 | 100.5 | 100.8 | 99.9 |
| Additional parameter | | | | |
| Resistance to crushing [N] [7] | t: ≥90 | 221 | 232 | 245 |

Figure 5:
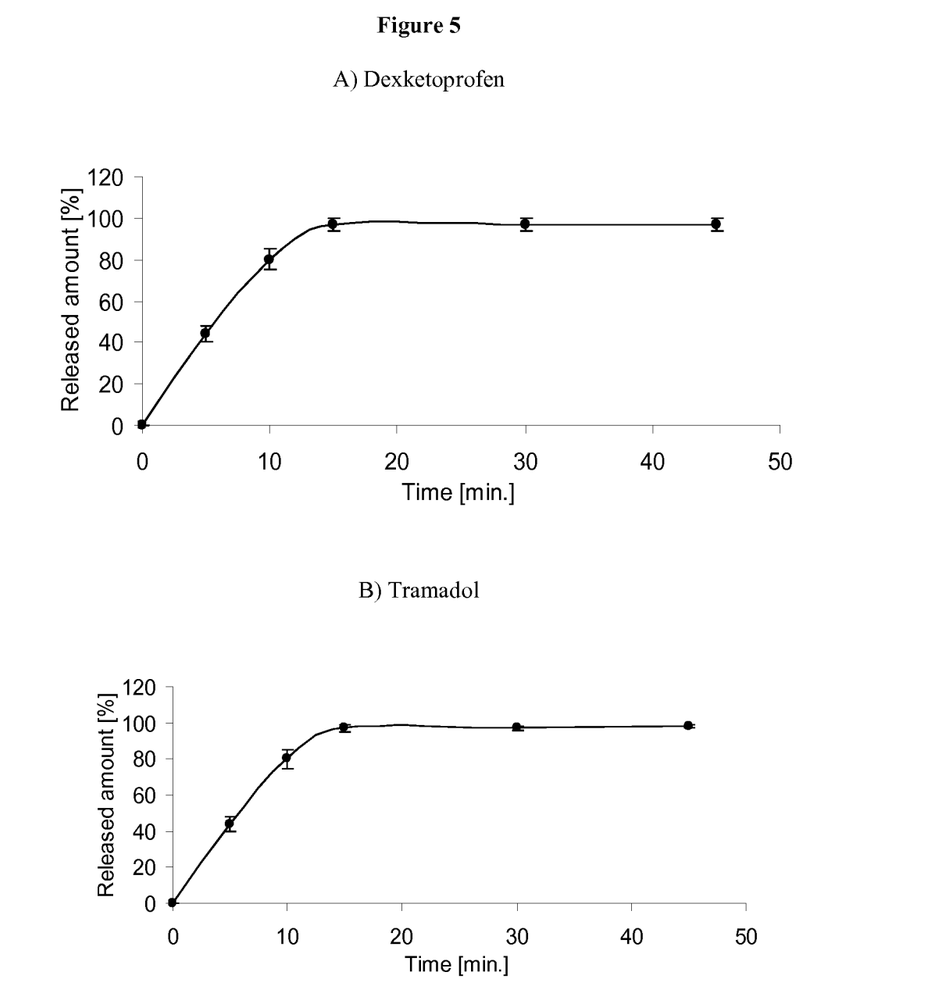
FIG. 5: shows the dissolution profile of the film-coated tablets of dexketoprofen trometamol and tramadol hydrochloride originated from the first manufactured sub-batch of 100 Kg at the initial conditions.

The dissolution profile of the obtained film-coated tablets is shown in FIG. 5 and is comparable to that of the sample and pilot size batches.

The invention claimed is:

1. A pharmaceutical composition in a solid oral dosage form, comprising:
   i) a combination of the two active pharmaceutical ingredients, dexketoprofen as a salt with organic or inorganic bases and tramadol as a salt with organic or inorganic acids, wherein:
      the organic or inorganic base is selected from the group consisting of trometamol, trimethylamine, dimethylamine, ethylamine, trimethylamine, diethylamine, L-lysine, L-arginine, diethanolamine, sodium hydroxide,
      the organic or inorganic acid is selected from the group consisting of hydrochloric, hydrobromic, phosphoric, sulfuric, methanesulfonic, benzenesulfonic, toluenesulfonic, acetic, propionic, malic, maleic, succinic, citric, L-tartaric, lactic, malonic, aspartic, glutamic;
   ii) a filler which is microcrystalline cellulose;
   iii) a binder selected from the group consisting of maize starch, maize starch pregelatinized and hypromellose, or mixtures thereof;
   iv) a pharmaceutically acceptable excipient,
   wherein the two active ingredients form a homogeneous mixture in which said active ingredients are intimately mixed.

2. A pharmaceutical composition according to claim 1, wherein the organic base is trometamol and the inorganic acid is hydrochloric acid.

3. A pharmaceutical composition according to claim 1, wherein said pharmaceutical excipient is selected from disintegrant, lubricant and glidant.

4. A pharmaceutical composition according to claim 1, containing a mixture of the two active ingredients in a weight ratio of dexketoprofen to tramadol from 2:1 to 1:10, equivalent to a weight ratio of dexketoprofen trometamol to tramadol hydrochloride from 2.59:1 to 1:7.7.

5. A pharmaceutical composition according to claim 4, containing a mixture of the two active ingredients in a weight ratio of dexketoprofen to tramadol from 1:1 to 1:6, equivalent to a weight ratio of dexketoprofen trometamol to tramadol hydrochloride from 1.3:1 to 1:4.63.

6. A pharmaceutical composition according to claim 1 containing the two active ingredients, dexketoprofen and tramadol or salts thereof, in the following amounts for each oral dosage unit:
dexketoprofen from 8 to 50 mg, equivalent to dexketoprofen trometamol from 11.8 to 73.8 mg;
tramadol from 17.6 to 105.4 mg, equivalent to tramadol hydrochloride from 20 to 120 mg.

7. A pharmaceutical composition according to claim 6, containing the two active ingredients, dexketoprofen and tramadol or salts thereof, in the following amounts, for each oral dosage unit:
dexketoprofen from 10 to 30 mg, equivalent to dexketoprofen trometamol from 14.8 to 44.29 mg;
tramadol from 26.3 to 87.8 mg, equivalent to tramadol hydrochloride from 30 to 100 mg.

8. A pharmaceutical composition according to claim 1, containing the two active ingredients, dexketoprofen and tramadol or salts thereof, in the following specific amounts for each oral dosage unit:
dexketoprofen 12.5 mg or 25 mg, equivalent to dexketoprofen trometamol 18.45 mg or 36.95 mg;
tramadol 32.9 mg or 65.9 mg, equivalent to tramadol hydrochloride 37.5 mg or 75 mg.

9. A pharmaceutical composition according to claim 1, wherein microcrystalline cellulose is in a concentration range from 45 to 75% by weight of the total amount.

10. A pharmaceutical composition according to claim 1, wherein the binder is selected from the group consisting of maize starch, maize starch pregelatinized and hypromellose or mixtures thereof, in amounts from 7% to 12% by the total weight of the composition.

11. A pharmaceutical composition according to claim 1, further comprising a disintegrant which is selected from croscarmellose sodium and sodium starch glycolate or mixtures thereof, in amounts from 4% to 14% by the total composition weight.

12. A pharmaceutical composition according to claim 1, wherein the dissolution of the two active ingredients, dexketoprofen and tramadol, occurs in a time range between 3 and 11 minutes.

13. A pharmaceutical composition according to claim 1, wherein the dissolution rate and the purity profile of the components remain unchanged during shelf-life of 18 months at (25±2° C. and (60±5)% relative humidity in aluminium-aluminium and PVC/PVDC packages.

14. A pharmaceutical composition according to claim 1, which is in the form of tablet for immediate release of the active principles.

15. A pharmaceutical composition according to claim 14, wherein said tablet comprises a hypromellose based outer film coating.

16. A pharmaceutical composition according to claim 14, comprising a polyvinyl alcohol based outer film coating.

17. A pharmaceutical composition according to claim 1, which is in the form of a capsule for the immediate-release of both active principles.

18. A method of treating acute pain related to the following conditions: headache, toothache, inflammations and migraine, the method comprising administering to a patient in need thereof the pharmaceutical composition according to claim 1.

19. A method of manufacturing a pharmaceutical composition in accordance with claim 1, said method comprising fluid bed granulation and fluid bed drying of a mixture of active principles and excipients.

20. A pharmaceutical composition in a solid oral dosage form, comprising:
i) a combination of the two active pharmaceutical ingredients, dexketoprofen as a salt with organic or inorganic bases and tramadol as a salt with organic or inorganic acids, wherein:
the organic or inorganic base is selected from the group consisting of trometamol, trimethylamine, dimethylamine, ethylamine, trimethylamine, diethylamine, L-lysine, L-arginine, diethanolamine, sodium hydroxide,
the organic or inorganic acid is selected from the group consisting of hydrochloric, hydrobromic, phosphoric, sulfuric, methanesulfonic, benzenesulfonic, toluenesulfonic, acetic, propionic, malic, maleic, succinic, citric, L-tartaric, lactic, malonic, aspartic, glutamic;
ii) a filler which is microcrystalline cellulose;
iii) a binder selected from the group consisting of maize starch, maize starch pregelatinized and hypromellose, or mixtures thereof;
iv) a pharmaceutically acceptable excipient,
wherein the two active ingredients form a homogeneous and physico-chemical interaction-free mixture in which said active ingredients are intimately mixed.

21. The pharmaceutical composition of claim 1, wherein the pharmaceutical composition has a disintegration time of below 15 minutes when stored for two weeks at 60° C.

* * * * *

UNITED STATES PATENT AND TRADEMARK OFFICE
CERTIFICATE OF CORRECTION

PATENT NO. : 9,949,940 B2  
APPLICATION NO. : 14/767424  
DATED : April 24, 2018  
INVENTOR(S) : Reinhard Schmitz et al.

Page 1 of 1

It is certified that error appears in the above-identified patent and that said Letters Patent is hereby corrected as shown below:

- Assignee reads:  
Labortorios Mena Rini SA, Badalona (ES)

- Assignee should read:  
Labortorios Menarini SA, Badalona (ES)

Signed and Sealed this  
Twenty-eighth Day of August, 2018

Andrei Iancu  
*Director of the United States Patent and Trademark Office*